Figure 1:
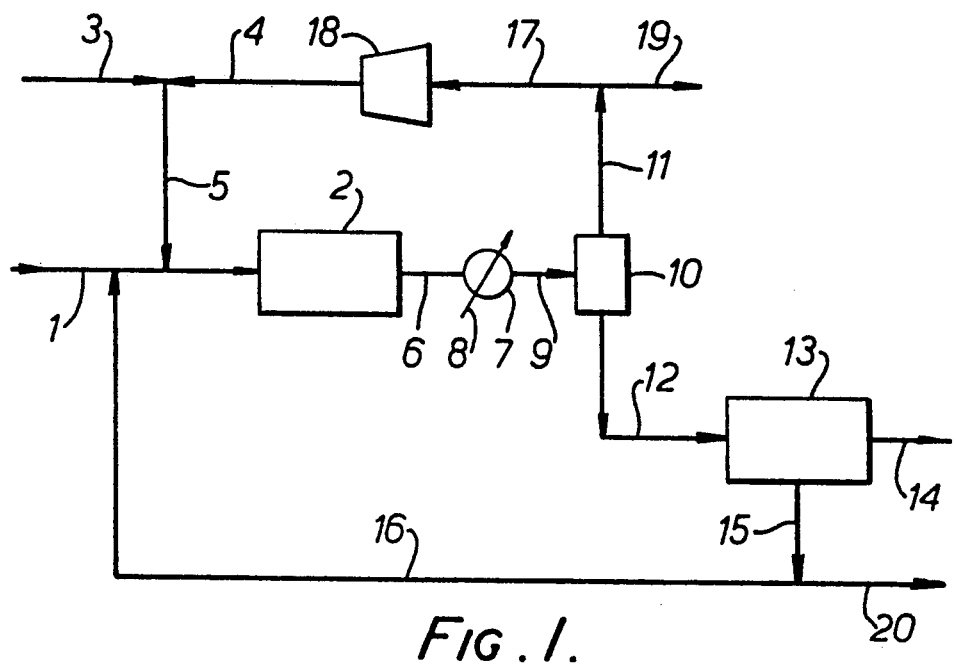

United States Patent [19]

Bradley et al.

[11] Patent Number: 5,004,845
[45] Date of Patent: Apr. 2, 1991

[54] HYDROGENATION OF ALDEHYDES

[75] Inventors: Michael W. Bradley, Marton; Norman Harris, Norton; Keith Turner, Fairfield, all of England

[73] Assignee: Davy McKee (London) Limited, London, England

[21] Appl. No.: 212,113

[22] Filed: Jun. 27, 1988

Related U.S. Application Data

[63] Continuation of Ser. No. 874,805, Jun. 13, 1986, abandoned, which is a continuation of Ser. No. 659,904, Oct. 11, 1984, abandoned, which is a continuation-in-part of Ser. No. 409,933, Aug. 20, 1982, abandoned, which is a continuation-in-part of Ser. No. 294,519, Aug. 20, 1981, abandoned.

[51] Int. Cl.⁵ .................. C07C 29/136; C07C 29/14; C07C 31/12; C07C 31/125
[52] U.S. Cl. .................. 568/885; 568/881; 568/914
[58] Field of Search .................. 568/885, 881, 914

[56] References Cited

U.S. PATENT DOCUMENTS

| | | | |
|---|---|---|---|
| 2,079,414 | 5/1937 | Lazier | 568/885 |
| 2,305,104 | 12/1942 | Pardee, Jr. | 260/635 |
| 2,543,038 | 2/1951 | McGrath | 260/450 |
| 2,549,416 | 9/1951 | Brooks | 568/881 |
| 3,729,520 | 4/1973 | Rutzen et al. | 260/638 |
| 3,923,694 | 12/1975 | Cornthwaite | 252/463 |
| 3,971,735 | 7/1976 | Asano et al. | 252/432 |
| 4,052,467 | 10/1977 | Mills et al. | 260/638 |
| 4,199,479 | 4/1980 | Wilkes | 252/457 |

FOREIGN PATENT DOCUMENTS

| | | |
|---|---|---|
| 853937 | 10/1977 | Belgium . |
| 8767 | 3/1980 | European Pat. Off. ............ 568/881 |
| 046983 | 3/1982 | European Pat. Off. . |
| 060787 | 9/1982 | European Pat. Off. . |
| 2613226 | 9/1977 | Fed. Rep. of Germany . |
| 417582 | 1/1933 | United Kingdom . |
| 555240 | 8/1943 | United Kingdom . |
| 575380 | 2/1946 | United Kingdom . |

OTHER PUBLICATIONS

Ullmanns Encyklopadie der Technischen Chemie, vol. II, pp. 431-434, w/translation.
Practical Catalytic Hydrogenation, Wiley & Sons, Inc., New York, N.Y., p. V.

Primary Examiner—J. E. Evans
Attorney, Agent, or Firm—Bernard, Rothwell & Brown

[57] ABSTRACT

Aliphatic aldehydes are hydrogenated to alcohols containing by product ester which ester is removed and separately hydrogenated to provide additional product.

17 Claims, 1 Drawing Sheet

HYDROGENATION OF ALDEHYDES

This is a continuation of application Serial No. 874,805, filed June 13, 1986—which is a continuation of application Serial No. 659,904 filed October 11, 1984—which is a continuation-in-part of application Serial No. 409,933 filed August 20, 1982 which is a continuation-in-part of application Serial No. 294,519 filed August 20, 1981, all now abandoned.

This invention relates to catalytic hydrogenation more particularly to catalytic hydrogenation of aliphatic aldehydes.

Catalytic hydrogenation of aldehydes to form the corresponding alcohol is a well known reaction and is widely practised on a commercial scale. For example, n-butyraldehyde which is conventionally produced by oxo synthesis from propylene is catalytically hydrogenated on a large scale to form n-butanol, whilst 2-ethylpropylacrolein formed, for example by aldolisation of n-butyraldehyde to form 2-ethyl-3-hydroxyhexanal followed by dehydration, is reduced in considerable tonnage annually to form the plasticiser alcohol 2-ethylhexanol.

Vapour phase hydrogenation of aliphatic aldehydes, such as 3,5,5-trimethylhexanal, using a catalyst comprising reduced copper plus zinc oxide is described in U.S. Pat. No. 2549416. Temperatures in the range of from 150° C. to 250° C. and pressures of from 200 to 600 p.s.i.g. (about 15 to about 43 kg/cm$^2$ absolute) are recommended. The 3,5,5-trimethylhexanal is typically prepared by hydroformylation of diisobutylene (i.e. a mixture of 2,4,4-trimethyl-1-pentene and 2,4,4-trimethyl-2-pentene) using a cobalt naphthenate catalyst to produce a crude product containing 63% of the desired aldehyde, 12% miscellaneous material, 12% isooctane, and 13% unreacted diisobutylene. This is then distilled to produce substantially pure aldehyde or treated by steam or vacuum distillation to produce a semi-refined aldehyde fraction containing 77% 3,5,5-trimethylhexanal and 7.3% 3,5,5-trimethylhexanoic acid. Either the crude, semi-refined, or the refined aldehyde is used as the raw material for the hydrogenation process. The prior art teaches increasing alcohol yield by using the crude or semi-refined fraction which contain substances, in addition to the aldehyde itself, which are converted by hydrogenation to the desired alcohol, i.e. 3,5,5-trimethylhexanol; these substances include 3,5,5-trimethylhexanoic acid and 3,5,5-trimethylhexyl formate as well as "various other esters, acetals, etc", but the "various other esters" are not identified, although it can be surmised that these are also formate esters, possibly derived, for example, from alcohols that are isomeric to the desired 3,5,5-trimethylhexanol. Specific compositions given for the crude and semi-refined aldehyde fractions do not mention any ester components, leading to the conclusion that the ester content of either composition must be minimal. Further, it is taught that the life of the copper-zinc oxide catalyst is longer when using the purified aldehyde. This leads to the conclusion that one or more minor components of the crude or semi-refined aldehyde fractions, perhaps 3,5,5-trimethylhexyl formate or one of the "various other esters" acts as a catalyst poison or deactivator. As Example 1 teaches hydrogenation of a refined aldehyde fraction containing, in addition to 3,5,5-trimethylhexanal, from 1 to 3% of 3,5,5-trimethylhexanoic acid, wherein the catalyst life exceeds 300 hours without loss of catalyst activity, it would appear that 3,5,5-trimethylhexanoic acid is not the material responsible for catalyst poisoning or deactivation. Of the other materials mentioned as components of the crude or semi-refined aldehyde fraction, it seems unlikely that an acetal, which is a labile adduct of an aldehyde and an alcohol can be the compound responsible for loss of catalyst activity. Hence one skilled in the art would deduce that the ester components of the crude or semi-refined fraction are the probable culprits in reducing the catalyst life. Hydrogenolysis of esters is described in U.S. Pat. No. 2079414. This teaches use of a copper catalyst which may be promoted with oxide promoters such as manganese oxide, zinc oxide, magnesium oxide or chromium oxide. In one Example liquid n-butyl butyrate is converted to n-butyl alcohol using an 8:1:1 by weight mixture of copper oxide, zinc oxide and magnesium oxide, at a conversion of about 50% of the ester to alcohol, at a hydrogen-ester molecular ratio of about 10:1, at a temperature of 322° C. and at a pressure of 2680 lbs. per square inch (about 189.4 kg/cm$^2$). It is taught that the best conversions to alcohols are obtained at the highest pressures obtainable in the available equipment and at the lowest temperatures consistent with obtaining a practical rate of reaction. Although operation in the "vapour phase" is mentioned, it is apparent that operation at temperatures in excess of the critical temperature of the ester is intended. This is confirmed by the teaching that in operating in the vapour phase it is preferred to use temperatures within the range of 300° C. to 400° C. The most preferred catalysts are those containing copper oxide promoted by chromium oxide either in physical mixture or in chemical combination as copper chromate or copper chromite. Hence the prior art teaches the superiority of chromium oxide to other oxide promoters such as zinc oxide.

In processes for effecting catalytic hydrogenation of aliphatic aldehydes a by-product may be an ester containing twice as many carbon atoms as the aldehyde. Such esters contain the same number of carbon atoms in the acid radical as in the alcohol radical and are quite different from the asymetric formate esters, such as 3,5,5-trimethylhexyl formate, mentioned in the aforementioned U.S. Pat. No. 2549416. For example, when using certain hydrogenation catalysts, n-propyl propionate is a by-product of hydrogenation of propionaldehyde and n-butyl butyrate can be detected in minor amounts in the reaction mixture resulting from catalytic hydrogenation of n-butyraldehyde. Thus European Patent Publication No. 0008767 mentions that when hydrogenating propionaldehyde in the vapour phase over a solid catalyst comprising a reduced mixture of CuO and ZnO a minor by-product is propyl propionate; similarly n-butyl butyrate is formed in minor amounts when n-butyraldehyde is hydrogenated under similar conditions. The formation of even a small percentage of esters, such as n-butyl butyrate, represents a serious loss in the potential yield of product alcohol, e.g. n-butanol. Such losses may render use of a particular hydrogenation catalyst, which otherwise has many advantageous properties, commercially unattractive.

Usually the amount of by-product ester formed increases with increasing temperature in the catalytic hydrogenation zone. Hence, in order to minimize formation of by-product ester, it is necessary to operate the catalytic hydrogenation zone at a relatively low temperature, which may in turn result in a somewhat reduced rate of catalytic hydrogenation and hence an increase in catalyst volume and in reactor size. Moreover, since catalyst activity tends to decline in use as time passes, it is usually necessary to raise the reaction temperature gradually with passage of time over a period of months of continuous operation in order to compensate for loss of catalytic hydrogenation activity. Such increase in temperature means that the amount of by-product ester formed increases so that eventually it becomes necessary to change the catalyst charge, because the level of by-product ester formation can no longer be tolerated, even though the original catalyst charge is still effective for aldehyde hydrogenation and would otherwise have many months of catalytic activity despite continuous operation.

There is therefore a need to provide a process for catalytic hydrogenation of aliphatic aldehydes to form the corresponding alcohols using hydrogenation catalysts, which otherwise tend to give rise to formation of by-product esters, wherein the effect of by-product ester formation is substantially eliminated or minimised, so as to maximise conversion of aldehyde to alcohol and to maximise the yield of alcohol based upon starting aldehyde.

There is also a need to extend the life of aldehyde hydrogenation catalysts whilst minimising losses of product through by-product ester formation.

Yet another need is to enable aldehyde hydrogenation catalysts to be used at higher than normal reaction temperatures in the hydrogenation of aliphatic aldehydes without increasing losses through by-product ester formation.

The present invention accordingly seeks to provide a process for catalytic hydrogenation of aliphatic aldehydes containing from 2 to about 10 carbon atoms wherein potential loss of product alcohol by way of by-product ester formation is minimised. The invention further seeks to provide a process for the production of an aliphatic alcohol containing from 2 to about 10 carbon atoms by catalytic hydrogenation of an aliphatic aldehyde containing from 2 to about 10 carbon atoms in which at least a major part of the by-product ester formed is converted to product alcohol. The present invention also seeks to provide a catalytic hydrogenation process in which an aliphatic $C_2$ to $C_{10}$ aldehyde is reduced to an aliphatic $C_2$ to $C_{10}$ alcohol with concomitant production of by-product ester wherein by-product ester is recovered and converted to two moles of product alcohol per mole of ester, thereby maximising the yield of product alcohol.

It also seeks to provide an aliphatic $C_2$ to $C_{10}$ aldehyde hydrogenation process in which catalyst life is substantially extended for further months of continuous operation and in which operation at higher than usual temperatures is permitted whilst minimizing losses of potential product through by-product ester formation.

According to one aspect of the present invention there is provided, in a continuous process for the production of an aliphatic alcohol containing from 2 to about 10 carbon atoms by catalytic hydrogenation of an aliphatic aldehyde containing from 2 to about 10 carbon atoms by reaction of a hydrogenation mixture containing the aldehyde and hydrogen in a catalytic aldehyde hydrogenation zone containing a charge of a hydrogenation catalyst effective for the hydrogenation of aldehydes and maintained under aldehyde hydrogenation conditions, followed by recovery of a reaction mixture containing, in addition to product alcohol, a minor amount of a by-product ester containing twice as many carbon atoms as the product alcohol, the improvement comprising separating by-product ester from the reaction mixture, and contacting an essentially aldehyde-free vaporous mixture comprising by-product ester and hydrogen, in which mixture the vapour pressure of said by-product ester is at least about 0.05 $kg/cm^2$, preferably at least about 0.1 $kg/cm^2$, and more preferably at least about 0.2 $kg/cm^2$, in a secondary catalytic hydrogenation zone with a catalyst consisting essentially of a reduced mixture of copper oxide and zinc oxide, at a temperature in the range of from about 150° C. to about 240° C., preferably from about 160° C. to about 220° C. and at a pressure in the range of from about 5 $kg/cm^2$ absolute up to about 50 kg./$cm^2$ absolute.

Amongst hydrogenation catalysts that have been suggested for catalytic hydrogenation of aliphatic aldehydes to give the corresponding aliphatic alcohols, there may be mentioned catalysts such as nickel, cobalt, molybdenum sulphide, copper chromite, and the like. Such catalysts generally give rise to minor amounts of "heavies", i.e. materials having boiling points higher than the aldehyde starting material or the product alcohol. Amongst such "heavies" there may in some cases be present an ester, usually an alkyl ester of an alkylcarboxylic acid, which ester contains twice as many carbon atoms as the starting aldehyde; for example when hydrogenating n-butyraldehyde to n-butanol, the "heavies" by-products may include the ester n-butyl butyrate.

As a particular example of a hydrogenation catalyst that may be used in the catalytic aldehyde hydrogenation zone and which is effective for the hydrogenation of aliphatic aldehydes in the vapour phase, there may be mentioned a reduced mixture of copper oxide and zinc oxide. When such a catalyst is used for catalytic hydrogenation of an aliphatic aldehyde, an ester is often detectable in the reaction product mixture. For example a minor amount of n-butyl butyrate may be present in the reaction product mixture obtained upon catalytic hydrogenation of n-butyraldehyde to n-butanol. Our investigations have shown that, with this catalyst, the ester formation reaction is reversible and that the reaction product mixture may contain up to about 2 percent or more by weight of ester by-product. The mechanism of formation of the ester is not entirely clear but the currently available evidence is consistent with a mechanism whereby two molecules of n-butyraldehyde react together to form n-butyl butyrate by a Tischenko reaction.

The catalytic hydrogenation of aldehydes containing 1 to 8 carbon atoms in the vapour phase using a reduced mixture of copper oxide and zinc oxide is described in more detail in European Patent Publication No. 0008767 (European Patent Application No. 79103181.8 filed 28th August 1979 by Union Carbide Corporation), the disclosure of which is herein incorporated by reference. The catalytic hydrogenation of the aldehyde may be conducted in a cooled tubular or multi-tubular reactor or in an adiabatic reactor. Usually it will be expedient to conduct the catalytic hydrogenation of the aldehyde to the alcohol in the presence of excess hydrogen. Typically the hydrogen aldehyde molar ratio lies in the range of from about 5:1 to about 100:1, more preferably in the range of from about 20:1 to about 60:1.

The process of the invention is applicable to the hydrogenation of aliphatic aldehydes, for example, alkyl, alkenyl or alkynyl aldehydes, which contain from 2 to about 10 carbon atoms, or mixtures of such aldehydes.

Such aldehydes preferably contain from 2 to about 8 carbon atoms. Typical aldehydes include acetaldehyde, propionaldehyde, n- and iso-butyraldehydes, n- and iso-valeraldehyde, n-hexaldehyde, n-heptaldehyde, n-octanal, 2-ethylhexanal, 2-ethylhex-2-enal (2-ethyl propyl acrolein), n-decanal, 2-ethylbutanal, propargyl aldehyde, acrolein, crotonaldehyde, alpha-citronellal, citral, trimethylacetaldehyde, diethylacetaldehyde, and the like, as well as mixtures thereof.

The aliphatic aldehyde or aldehydes used as starting material may be supplied to the catalytic aldehyde hydrogenation zone as such or in admixture with inert vaporisable materials such as alcohols.

In the catalytic aldehyde hydrogenation zone the hydrogen:aldehyde molar ratio preferably lies in the range of from about 2:1 to about 100:1, more preferably in the range of from about 5:1 to about 60:1. The temperature will usually lie in the range of from about 75° C. to about 300° C., and will usually exceed about 100° C. It will lie preferably in the range of from about 150° C. to about 240° C. The pressure in the catalytic aldehyde hydrogenation zone will usually be in the range of from about 0.1 kg/cm² absolute to about 100 kg/cm² absolute. Preferably the pressure is at least about 1 kg/cm² absolute up to about 60 kg/cm² absolute and even more preferably lies in the range of from about 5 to about 50 kg/cm². The pressure is most preferably not more than about 25 kg/cm² absolute.

When using a catalyst of the type described in the aforementioned European Patent Publication No. 0008767, it is essential that the aldehyde be supplied in vapour form to the catalytic aldehyde hydrogenation zone. This requires that the reaction conditions in the catalytic aldehyde hydrogenation zone shall be such that the aldehyde is always maintained above its dew point under the prevailing pressure and temperature conditions as well as below its critical pressure and temperature.

The reaction mixture exiting the catalytic aldehyde hydrogenation zone in the process of the invention contains, in addition to product alcohol, a minor amount of ester by-product. In one preferred process the aldehyde is selected from n-butyraldehyde, iso-butyraldehyde, and mixtures thereof, the by-product ester is selected from n-butyl butyrate, iso-butyl butyrate, n-butyl iso-butyrate and iso-butyl iso-butyrate, and mixtures thereof, and the product alcohol selected from is n-butanol, iso-butanol, and mixtures thereof. In another preferred process the aldehyde is propionaldehyde, the by-product ester is n-propyl propionate, and the product alcohol is n-propanol. Yet again the aldehyde may be 2-ethylpropylacrolein, in which case the by-product ester is 2-ethylhexyl 2-ethylhexanoate, and the product alcohol is 2-ethylhexanol.

If a mixture of aldehydes is used as starting material, then a mixture of alcohols will be formed and a mixture of ester by-products may be produced. For example, when using a mixture of n- and iso-butyraldehydes as starting material, the alcohol product fraction includes both n- and iso butanols and a mixture of by-product esters is formed, viz. a mixture of n-butyl butyrate, iso-butyl butyrate, n-butyl iso-butyrate and iso-butyl iso-butyrate. Since the or each ester by-product has a molecular weight approximately twice that of the aldehyde and of the product alcohol, the boiling points of such esters are significantly higher than that of the aldehyde and of the product alcohol. Hence it will usually be convenient to recover the product alcohol or alcohols from the reaction mixture and to separate ester by-product or by-products therefrom by distillation in each case. Distillation can be effected in one or more stages under normal, reduced or elevated pressure.

In the catalytic aldehyde hydrogenation step one mole of hydrogen is consumed upon reduction of an aldehyde group —CHO to a primary alcohol group —CH$_2$OH. If the aldehyde starting material contains in addition ethylenic unsaturation, a further mole of hydrogen may be consumed by reduction of the ethylenic unsaturation in the catalytic aldehyde hydrogenation zone. Hence two moles of hydrogen are consumed upon reduction of an unsaturated aldehyde such as 2-ethylhex-2-enal (2-ethylpropylacrolein) to the corresponding alcohol, e.g. 2-ethylhexanol. If the aldehyde contains acetylenic unsaturation, two moles of hydrogen are consumed upon reduction of the acetylenic linkage. For example catalytic hydrogenation of propargyl aldehyde to n-propanol will consume three moles of hydrogen.

According to a preferred procedure, by-product ester separated from the reaction product mixture exiting the catalytic hydrogenation zone is recycled to the inlet end of the catalytic hydrogenation zone and vaporised prior to entry thereto. After a period of steady state operation the concentration of ester by-product in the reaction product mixture exiting the catalytic aldehyde hydrogenation zone approaches an equilibrium concentration. Hence, if all the by-product ester is recycled to the inlet end of the catalytic hydrogenation zone, the concentration of ester vapour in the hydrogenation mixture at the inlet end of the catalytic hydrogenation zone also approaches the equilibrium value so that the overall conversion of aldehyde to ester is minimised. If no bleed streams are taken to control the composition of the ester recycle stream, then the overall conversion of aldehyde to ester in the catalytic aldehyde hydrogenation zone approaches zero.

Hence, according to another aspect of the present invention, there is provided, in a continuous process for the production of an aliphatic alcohol containing from 2 to about 10 carbon atoms by catalytic hydrogenation of an aliphatic aldehyde containing from 2 to about 10 carbon atoms by reaction of a hydrogenation mixture containing vaporous aldehyde, a minor amount of vaporous ester and hydrogen in a catalytic aldehyde hydrogenation zone maintained under elevated pressure and at a temperature in the range of from about 150° C. to about 240° C., preferably from about 160° C. to about 220° C. and containing a charge of a hydrogenation catalyst consisting essentially of a reduced mixture of copper oxide and zinc oxide, followed by recovery of a reaction mixture containing product alcohol, the improvement comprising separating from the reaction mixture a minor amount of a by-product ester containing twice as many carbon atoms as the product alcohol, recycling separated by-product ester to the inlet end of the aldehyde hydrogenation zone to provide a minor amount of ester for incorporation in the hydrogenation mixture, and vaporising said recycled by-product ester prior to entry to the catalytic aldehyde hydrogenation zone, thereby to establish at the inlet end of the catalytic aldehyde hydrogenation zone a vaporous concentration of said by-product ester in the hydrogenation mixture that approaches an equilibrium value and hence to minimise overall conversion of aldehyde to by-product ester, the hydrogenation zone preferably being operated adiabatically and being maintained at a pressure in the range of from about 5 kg/cm$^2$ absolute up to about 50 kg/cm$^2$ absolute.

As already mentioned, by-product ester is conveniently separated from the reaction product mixture exiting the catalytic aldehyde hydrogenation zone by distillation. If the ester forms an azeotrope with one or more other components of the reaction product mixture, it is not necessary to separate this azeotrope which can be recycled as such to the inlet end of the catalytic aldehyde hydrogenation zone.

In an alternative preferred procedure ester by-product separated from the reaction product mixture from the catalytic aldehyde hydrogenation zone is contacted in a secondary catalytic hydrogenation zone, which acts as a separate ester hydrogenolysis zone, with the ester hydrogenolysis catalyst (i.e. the reduced mixture of oxides consisting essentially of copper oxide and zinc oxide). In this case it is preferred to operate the two hydrogenation zones at essentially the same pressure or to operate the secondary catalytic hydrogenation zone at a lower pressure than the catalytic aldehyde hydrogenation zone. In this way it is not necessary in either case to recompress the gas between the two zones.

Upon contact of the vaporous by-product ester with the catalyst consisting essentially of copper oxide and zinc oxide, whether this occurs in the catalytic aldehyde hydrogenation zone or in a separate ester hydrogenolysis zone, hydrogenolysis occurs. Generally, both the acid moiety and alcohol moiety of the ester group appear as alcohol in the reaction product mixture. Thus, for example, n-butyl butyrate formed as by-product in the reduction of n-butyraldehyde is smoothly converted to two moles of n-butanol upon contact with the hydrogenolysis catalyst in the presence of hydrogen under the specified reaction conditions.

The hydrogenolysis of esters is disclosed in our copending International Patent Application No. PCT/GB 82/00118 filed 21st April 1982 now published as International Patent Publication No. WO82/03854, which is equivalent to our co-pending U.S. patent application Ser. No. 433201 filed 30th September 1982. The entire disclosure of those co-pending applications is herein incorporated by reference.

In the catalytic aldehyde hydrogenation zone, as well as in the separate ester hydrogenolysis zone (if this is used), the vaporous mixture that is contacted with the catalyst contains, in addition to by-product ester, hydrogen either alone or in admixture with other gases (desirably gases inert to the ester and the catalyst). In this mixture the ester is in vapour form. Hence the conditions are selected so that the ester is always maintained above its dew point, as well as below its critical temperature and pressure. The gaseous mixtures containing hydrogen may include essentially inert gases such as nitrogen.

The hydrogenolysis conditions used in the secondary catalytic hydrogenation zone are surprisingly mild compared with conventional ester hydrogenolysis conditions and yield almost quantitative amounts of alcohol, often in excess of 99% yield, at high rates of conversion, often also in excess of 99%. Moreover the results from use of a catalyst consisting essentially of a reduced mixture of copper oxide and zinc oxide are completely unexpected in view of the prior art teaching that catalysts containing chromium, particularly copper chromate and chromite, are superior to copper oxide catalysts containing other oxide promoters including zinc oxide. The ester hydrogenolysis catalyst, i.e. a mixture consisting essentially of a reduced mixture of copper oxide and zinc oxide, is marked by excellent catalyst life and permits continuous operation for periods of many months without significant loss of catalytic activity for ester hydrogenolysis. Moreover the ester hydrogenolysis conditions used are remarkable for a marked absence of by-products of hydrogenolysis, such as alkanes etc. In addition there appears to be essentially no thermal degradation of the ester, such as may occur with formate esters, as the reaction mixture contains no more than trace amounts of carbon monoxide.

In the procedure according to the invention in which by-product ester is recycled to the inlet end of the aldehyde hydrogenation zone it is surprisingly found that the life of the catalyst is not affected adversely by the deliberate recycle of the ester. This is in direct contrast to the teachings of the afore-mentioned U.S. Pat. No. 2549416 which indicates that the presence of ester impurities in the aldehyde feed material has a deleterious effect on catalyst life and that for extended catalyst life it is necessary to use a purified aldehyde fraction.

The hydrogenolysis step of the process of the invention is conducted at a temperature of between about 150° C. and about 240° C., preferably in the range of from about 160° C. to about 220° C. The total pressure is between about 5 kg/cm$^2$ absolute and about 50 kg/cm$^2$ absolute. Preferably the pressure in the ester hydrogenolysis zone lies between about 5 kg/cm$^2$ absolute and about 25 kg/cm$^2$ absolute.

The catalyst of the hydrogenolysis step, which may be the same as the catalyst of the aldehyde hydrogenation zone, is a mixed metal oxide catalyst that consists essentially of a reduced mixture of copper oxide and zinc oxide. By the term "consists essentially of" we mean that the catalyst includes as essential ingredients in the mixture before reduction copper oxide and zinc oxide, but may also include incidental amounts of other metal oxides that do not materially alter the basic characteristics of the catalyst, and that it may also include inert fillers or supports, such as carbon. Such characteristics include the ability to catalyse hydrogenolysis of alkyl esters of aliphatic monocarboxylic acids, in the presence of an at least stoichiometric amount of hydrogen at moderate temperatures, for example in the range of from about 150° C. to about 240° C., and low pressures, for example in the range of from about 5 kg/cm$^2$ absolute, to about 50 kg/cm$^2$ absolute with high selectivity to the desired alcohol or alcohols, typically in excess of 90%, and with a marked absence of significant amounts of by-products, typically less than 1% in total of by-products, such as alkanes, alkenes, ethers, acids, aldehydes, and "heavies", and trace amounts only, if any, of CO. Such "heavies" may include, for example, higher alcohols having twice or three times as many carbon atoms as the desired alcohol.

The catalyst may be derived from a mixture which contains only copper oxide and zinc oxide. Alternatively it may include one or more other materials, such as an inert support or other material that is effectively catalytically inactive in the ester hydrogenolysis reaction.

Hence the catalyst may be derived from a mixture of CuO and ZnO, which before reduction contains from about 5 to about 95% by weight preferably from about 20 to about 85% by weight, and typically from about 25 to about 70% by weight, of CuO and from about 95 to about 5% by weight, preferably from about 80 to about 15% by weight and typically from about 75 to about 30% by weight, of ZnO. Hence the mixture may contain, for example, from about 20 to about 40% by weight of CuO and from about 60 to about 80% by weight of ZnO. A preferred mixture, for example contains from about 30 to about 36% by weight of CuO and from about 62 to about 68% by weight of ZnO. Other particularly preferred mixtures contain from about 65 to about 85% by weight of CuO and from about 35 to about 15% by weight of ZnO, for example mixtures containing from about 60 to about 75% (e.g. about 68 to about 75%) by weight of CuO and from about 40 to about 25% (e.g. about 32 to about 25%) by weight of ZnO.

As already mentioned the catalyst may contain minor amounts of at least one carrier material such as carbon, titanium oxide, zirconium oxide, manganese dioxide, silica, diatomaceous earth, kieselguhr, or aluminum oxide. Such carrier materials do not usually comprise in total more than about 20% by weight of the catalyst. The presence of minor amounts of other materials can be tolerated in the mixture from which the catalyst is derived, provided that these do not significantly affect the catalyst performance.

Other preferred catalysts include mixtures containing from about 40 to about 50 weight percent each of CuO and ZnO and from 0 to about 20 weight percent of alumina.

The catalyst may be prepared by any of the methods known in the art of forming a composite of copper oxide and zinc oxide. The catalyst may be prepared by fixing the separate oxides, by coprecipitation of the oxalates, nitrates, carbonates, or acetates, followed by calcination. The coprecipitation method is preferred. Generally, the mixture of CuO and ZnO is reduced by hydrogen or carbon monoxide at a temperature in the range of between about 160° C. and about 250° C. for several hours, preferably for 8 to 24 hours, prior to contact with the vaporous mixture containing by-product ester and hydrogen. If the catalyst is charged in a pre-reduced form the period required for reduction can be reduced accordingly.

The mixture of CuO and ZnO is reduced prior to its use as catalyst in the aldehyde hydrogenation step or in the ester hydrogenolysis step. Hydrogen or CO, or mixtures thereof, are generally mixed with a diluent gas such as steam, nitrogen, or combustion gas, to maintain the catalyst bed temperature and to carry away the heat of reduction.

Reduction of the mixture of CuO and ZnO is complete when no more hydrogen is being reacted as shown by analysis of the inlet and outlet hydrogen. Complete reduction of the mixture occurs when the total amount of water produced in the reduction is equal to the stoichiometric value of water which should be produced when a given amount of copper oxide is reduced to copper. This value is about 0.079 kg of water per kg of catalyst for a mixture containing 35 weight percent of CuO.

An inert carrier material may be included in the CuO-ZnO catalyst composition. The catalyst is generally formed into pellets, tablets, or any other suitable shape prior to use, by conventional techniques.

It is advantageous that the mixture of CuO and ZnO have an internal surface area of from about 25 to about 50 sq.m per gram. The internal surface area may be determined by the well-known BET method.

The reaction product mixture from the hydrogenolysis step may be separated from any excess hydrogen by condensation and the excess hydrogen can be compressed and recycled. This reaction product mixture comprises product alcohol in addition to a possible minor amount of unconverted ester by-product. This mixture is separated in any suitable manner, e.g. by distillation. The product alcohol may be used as recovered or it can be further purified in a conventional manner such as by fractional distillation. Preferably any unconverted by-product ester recovered is recycled to the hydrogenolysis stage.

In the hydrogenolysis step the partial pressure of the by-product ester is at least about 0.05 kg/cm$^2$, preferably at least about 0.1 kg/cm$^2$, and even more preferably at least about 0.2 kg/cm$^2$, and may vary within wide limits, e.g. from about 0.05 kg/cm$^2$ or less up to about 10 kg/cm$^2$ or more. Care must however be taken to ensure that at all times the temperature of the vaporous mixture in contact with the CuO—ZnO catalyst is above the dew point of the ester under the prevailing pressure conditions. In addition the conditions under which hydrogenolysis is being effected must be such that the critical temperature and pressure of the ester are not exceeded.

In order that the invention may be clearly understood and readily carried into effect, two preferred forms of plant utilising the process of the invention will now be described, by way of example only, with reference to the accompanying diagrammatic drawings, FIGS. 1 and 2 of which each illustrate a flow sheet of a plant for production of an alcohol by catalytic hydrogenation of an aldehyde.

It will be appreciated by those skilled in the art that, since the drawings are diagrammatic, various items of equipment which would be included in practice in an operational plant, such as valves, temperature measurement devices, pressure control devices, re-boilers and the like, have been omitted for the sake of clarity. Such standard items of equipment would be provided in accordance with conventional chemical engineering practice and form no part of the present invention.

Referring to FIG. 1 of the drawings, a mixture of n- and iso- butyraldehydes in a molar ratio of about 6:1 is supplied through line 1 to an aldehyde hydrogenation zone 2 containing a charge of a hydrogenation catalyst which is a reduced mixture of CuO and ZnO. Make up hydrogen is supplied by way of line 3 and is mixed with recycled hydrogen in line 4, the mixed gases flowing on in line 5. The resulting vaporous mixture of hydrogen and aldehydes containing, for example, a hydrogen:aldehyde molar ratio of about 35:1 enters the inlet end of hydrogenation zone 2, which is maintained at a pressure of, for example, about 10 kg/cm$^2$ absolute, and at an inlet temperature of, for example, about 150° C.

Aldehyde hydrogenation zone 2 may be an externally cooled tubular or multi-tubular reactor or an adiabatic or multi-stage adiabatic reactor with interstage cooling.

Hydrogenation of the aldehydes proceeds essentially to 100 percent conversion in aldehyde hydrogenation zone 2. The vaporous reaction mixture exiting aldehyde hydrogenation zone comprises, in addition to excess hydrogen, mainly n- and iso-butanols but also a minor proportion, usually in the range of from about 1 percent to about 2 percent by weight, of by-product esters (i.e. a mixture of n-butyl butyrate, together with lesser amounts of iso-butyl butyrate, n-butyl iso-butyrate and iso-butyl iso-butyrate), and traces of higher boiling compounds derived from self-condensation products of n- and iso-butyraldehydes. This mixture passes by way of line 6 to a cooler 7 in which n- and iso-butanols and the other condensible components are condensed against cooling water supplied in line 8. The resulting gas/liquid mixture flows on in line 9 to a catchpot separator 10 from which the excess hydrogen is withdrawn in line 11, whilst the crude liquid product mixture is passed on in line 12 to separation zone 13 which conveniently takes the form of a distillation zone. Product alcohols, i.e. a mixture of n-butanol and iso-butanol are recovered from separation zone 13 as an overhead product in line 14, whilst by-product esters (e.g. n-butyl butyrate and isomers thereof) and "heavies" are recovered in the bottoms product in line 15 and are recycled to the inlet end of hydrogenation zone 2 in line 16. As can be seen from FIG. 1, the by-product esters in line 16 are combined with the make up aldehyde(s) in line 1 and are vaporised with the aldehyde(s) prior to entry to aldehyde hydrogenation zone 2. Usually the vapour pressure of by-product ester in the hydrogenation mixture entering the aldehyde hydrogenation zone is at least about 0.05 kg/cm$^2$, and typically exceeds about 0.2 kg/cm$^2$. Any unconverted aldehyde is recovered together with the product alcohols in line 14 and can be separated therefrom in a downstream distillation zone (not shown) and recycled to the process.

The excess hydrogen in line 11 is recycled to the inlet end of aldehyde hydrogenation zone 2 by way of line 17 by means of recycle gas compressor 18 and by way of line 4. A gas purge stream is taken through line 19 in order to control the level of impurities and inerts in the recirculating gas, whilst the build up of "heavies" in the liquid recycle line 16 is controlled by taking a liquid purge through line 20.

Figure 2:
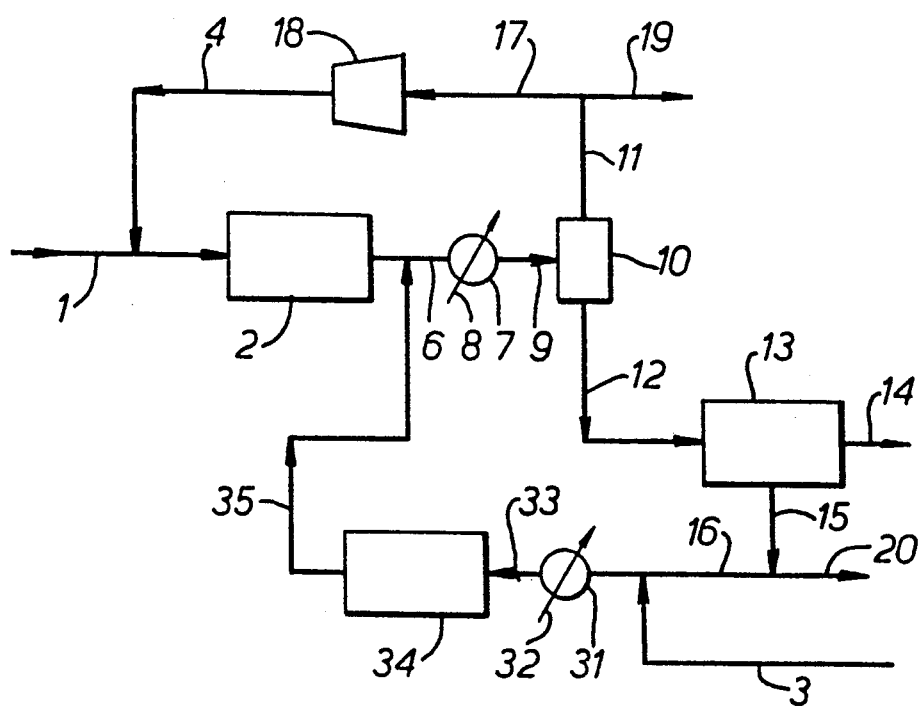

In FIG. 2 the same reference numerals are used as are used in FIG. 1 to denote like items of equipment. In this plant n-butyraldehyde is supplied in line 1 and the product alcohol is n-butanol, whilst the ester by-product is n-butyl butyrate. Make up hydrogen from line 3 is admixed with recycled n-butyl butyrate in line 16 and the resulting mixture is passed to vaporiser 31 which is heated by means of steam supplied in line 32. The resulting hydrogen/vaporous n-butyl butyrate mixture has a hydrogen:ester molar ratio of about 33:1 and passes on by way of line 33 to a secondary catalytic hydrogenation zone 34 containing the same catalyst as that used in zone 2 of each of FIGS. 1 and 2. The inlet temperature to the secondary catalytic hydrogenation zone is about 175° C. and the total pressure is about 9.0 kg/cm$^2$ absolute, whilst the vapour pressure, of the ester is about 0.26 kg/cm$^2$. This secondary catalytic hydrogenation zone 34 may comprise an externally cooled tubular or multi-tubular reactor or a single bed adiabatic reactor or a multi-bed adiabatic reactor, possibly with intercooling between beds. Hydrogenolysis of n-butyl butyrate to n-butanol occurs in zone 34 and the resulting vaporous hydrogen/n-butanol mixture is recovered in line 35 and admixed with the vaporous mixture in line 6. The unreacted hydrogen from zone 34, which comprises by far the major portion of the make-up hydrogen, as well as the excess hydrogen supplied to the inlet end of zone 2, is passed to the inlet end of the n-butyraldehyde hydrogenation zone 2 by way of line 9, catchpot separator 10, lines 11 and 17, recycle gas compressor 18 and line 4, being admixed upstream from the n-butyraldehyde hydrogenation zone 2 with n-butyraldehyde supplied by way of line 1. Product separation, product recovery, and provision for gas and liquid purge streams are as in the plant of FIG. 1.

The invention is further illustrated in the following Examples:

EXAMPLE 1 n-butyl butyrate was pumped at a rate of 3.8 ml/hr to an electrically heated gas/liquid mixing device to which hydrogen was also supplied at a controlled rate and pressure. The resulting vaporous mixture was passed through a lagged, electrically heated line to a pre-heating coil prior to passage through a tubular reactor packed with 146 ml of a powdered catalyst. Both the tubular reactor and the pre-heating coil were immersed in a molten salt bath which was heated to 174° C. The vaporous mixture exiting the reactor was passed through a water cooled condenser and the resulting condensate was collected in a water-cooled knock out pot. The exit gas pressure was controlled to 10.55 kg/cm$^2$ absolute. The non-condensed gases were then passed through a let-down valve, the gas flow being monitored downstream from this valve in a wet gas meter. A gas flow rate of 46.6 liters/hr (measured at atmospheric pressure) was maintained throughout the experiment. The ester partial pressure was 0.12 kg/cm$^2$ and the hydrogen:ester molar ratio was 84.3:1. The liquid hourly space velocity was 0.05 hr$^{-1}$.

The liquid condensate was analysed by gas chromatography using a 2 meter stainless steel column (6 mm outside diameter) packed with polyethylene glycol (nominal molecular weight 20,000) on Chromosorb PAW, a helium gas flow rate of 30 ml/minute and a flame ionisation detector. The instrument was fitted with a chart recorder having a peak integrator and was calibrated using a mixture of n-butanol and n-butyl butyrate of known composition. The condensate was shown to contain a mixture of 99.62 wt % butanol and 0.28 wt % n-butyl butyrate, corresponding to a 99.7% conversion with essentially 100% selectivity.

The catalyst used in this Example was charged to the reactor as a co-precipitated mixture of CuO and ZnO containing 33±3% CuO and 65±3% ZnO having a particle size in the range of 1.2 mm to 2.4 mm and an internal surface area of about 45 sq. m. per gram. This was pre-reduced in the reactor using a 5 vol % H$_2$ gas mixture at 200° C. for 17 hours followed by pure hydrogen at 200° C. for 8 hours, the gas flow rate in each case being about 20 liters/hr (measured at atmospheric pressure using the wet gas meter) and the gas pressure being 10.55 kg/cm$^2$ absolute. After this pre-reduction stage the catalyst was at all times maintained in a hydrogen-containing atmosphere.

EXAMPLES 2 AND 3

The general procedure of Example 1 was repeated using n-butyl butyrate under the condition specified in Table 1 below, which also lists the conversions and selectivities observed:

TABLE 1

|  | Example No. | |
|---|---|---|
|  | 2 | 3 |
| Temperature (°C.) | 175 | 200 |
| Total pressure in kg/cm$^2$ absolute | 9.0 | 9.0 |
| H$_2$:ester molar ratio | 33.0:1 | 33.0:1 |
| Ester partial pressure in kg/cm$^2$ | 0.26 | 0.26 |
| Liquid hourly space velocity (hr$^{-1}$) | 0.16 | 0.16 |
| Space velocity (hr$^{-1}$) | 1,500 | 1,500 |
| Conversion (%) | 82.0 | 95.0 |
| Selectivity to n-butanol (%) | 99 | 99 |

EXAMPLES 4 TO 7

Ethyl acetate was subjected to hydrogenolysis following an analogous method to that used in Example 1 using 50 ml of a powdered mixture containing, before reduction, 65% by weight CuO and 35% by weight ZnO. The conditions used and the results obtained are summarised in Table 2 below:

TABLE 2

|  | Example No. | | | |
|---|---|---|---|---|
|  | 4 | 5 | 6 | 7 |
| Temperature (°C.) | 162 | 194 | 150 | 250 |
| Ester liquid flow rate (ml/hr) | 23.0 | 21.4 | 21.7 | 21.7 |
| Exit gas pressure (kg/cm$^2$ absolute) | 38.67 | 70.31 | 11.60 | 11.6 |
| Gas flow rate (liters/hr) | 38 | 92 | 100 | 100 |
| H$_2$:ester molar ratio | 5.8:1 | 15.1:1 | 16.4:1 | 16.4:1 |
| Liquid hourly space velocity (hr$^{-1}$) | 0.46 | 0.43 | 0.43 | 0.43 |
| Ester partial pressure (kg/cm$^2$) | 5.7 | 4.4 | 0.67 | 0.67 |
| Conversion (%) | 43.8 | 90.7 | 45.7 | 91.0 |
| Selectivity to ethanol (%) | 99.8 | 99.8 | 100 | 100 |

EXAMPLE 8

A long term catalyst activity test was carried out under conditions which were selected to give a relatively low conversion per pass and hence permitted changes in activity of the catalyst to be mentioned readily. In this test there was used to hydrogen:ethyl acetate ester ratio of 10:1, a liquid hourly space velocity of 0.33 hr$^{-1}$ (corresponding to a total space velocity of 6200 hr$^{-1}$), a reaction temperature of 180° C. and a total pressure of 29.14 kg/cm$^2$ absolute. The partial pressure of ethyl acetate in the mixture was 2.6 kg/cm$^2$. The results are summarised in Table 3 below.

TABLE 3

| Time (hours) | % Conversion |
|---|---|
| 10 | 67 |
| 50 | 62 |
| 100 | 63 |
| 200 | 61 |
| 300 | 62 |
| 400 | 64 |
| 500 | 61 |
| 750 | 62 |
| 1000 | 63 |

These results show that, under vapour phase conditions used for ester hydrogenolysis, essentially no deactivation of the catalyst was observed over a period of 1000 hours, even under the non-optimum conditions selected. The catalyst was a reduced mixture containing, before reduction, 65% by weight CuO and 35% by weight ZnO.

EXAMPLE 9

The general procedure of Example 1 is repeated using n-propyl propionate and 2-ethylhexyl 2-ethylhexanoate. Similarly good yields are observed in each case.

What is claimed is:

1. In a continuous process for the production of an aliphatic alcohol containing 2 to 10 carbon atoms by catalytic hydrogenation of an aliphatic aldehyde containing 2 to 10 carbon atoms by reaction of a hydrogenation mixture containing the aldehyde and hydrogen in a catalytic aldehyde hydrogenation zone containing a charge of a hydrogenation catalyst effective for the hydrogenation of aldehydes and maintained under aldehyde hydrogenation conditions, followed by recovery of a reaction mixture containing, in addition to product alcohol, a minor amount of a by-product ester containing twice as many carbon atoms as the product alcohol, said ester being derived from an alkyl carboxylic acid containing the same number of carbon atoms as the product alcohol and from the product alcohol, the improvement comprising separating by-product ester from the reaction mixture and passing an essentially aldehyde-free vaporous mixture comprising by-product ester and hydrogen, in which mixture the vapour pressure of said by-product ester is at least about 0.05 kg/cm$^2$ over a catalyst consisting essentially of a reduced mixture of copper oxide and zinc oxide, in a secondary catalytic hydrogenation zone, at a temperature in the range of from about 150° C. to about 240° C. and at a pressure in the range of from about 5 kg/cm$^2$ absolute up to about 50 kg/cm$^2$ absolute, and recovering from said secondary catalytic hydrogenation zone a reaction mixture that is substantially free from by-product ester and contains a substantially quantitative yield of further product alcohol corresponding to 2 moles of further product alcohol per mole of by-product ester treated in the secondary catalytic hydrogenation zone.

2. A process according to claim 1, in which the aldehyde and the product alcohol each contain from 2 to about 8 carbon atoms.

3. A process according to claim 1, in which the aldehyde is selected from n-butyraldehyde, iso-butyraldehyde, and mixtures thereof, the by-product ester is selected from n-butyl butyrate, iso-butyl butyrate, n-butyl iso-butyrate and iso-butyl iso-butyrate, and mixtures thereof, and the product alcohol is selected from n-butanol, iso-butanol, and mixtures thereof.

4. A process according to claim 1, in which the aldehyde is propionaldehyde, the by-product ester is n-propyl propionate, and the product alcohol is n-propanol.

5. A process according to claim 1, in which the aldehyde is 2-ethylpropylacrolein, the by-product ester is 2-ethylhexyl 2-ethylhexanoate, and the product alcohol is 2-ethylhexanol.

6. A process according to claim 1, in which the hydrogenation catalyst of the catalytic aldehyde hydrogenation zone consists essentially of a reduced mixture of copper oxide and zinc oxide and in which the aldehyde in the hydrogenation mixture is in vaporous form.

7. A process according to claim 6, in which the catalytic aldehyde hydrogenation zone is maintained at a temperature in the range of from about 75° C. to about 300° C. and at a pressure in the range of from about 5 kg/cm² absolute up to about 50 kg/cm² absolute.

8. A process according to claim 1, in which make-up hydrogen is admixed with by-product ester separated from the reaction mixture, the excess hydrogen issuing from the secondary catalytic hydrogenation zone being supplied to the catalytic aldehyde hydrogenation zone.

9. A process according to claim 1, in which the hydrogen:aldehyde molar ratio in the aldehyde catalytic hydrogenation zone lies in the range of from about 2:1 to about 100:1.

10. A process according to claim 9, in which the hydrogen:aldehyde molar ratio lies in the range of from about 5:1 to about 60:1.

11. A process according to claim 1, in which the temperature in the secondary catalytic hydrogenation zone is in the range of from about 160° C. to about 220° C.

12. A process according to claim 1, in which the partial pressure of ester in the essentially aldehyde-free vaporous mixture is in the range of from about 0.2 kg/cm² up to about 10 kg/cm².

13. In a continuous process for the production of an aliphatic alcohol containing 2 to 10 carbon atoms by catalytic hydrogenation of an aliphatic aldehyde containing from 2 to 10 carbon atoms, which comprises:
   (i) vaporizing said aldehyde in a hydrogen-containing stream to form a hydrogenation mixture containing vaporous aldehyde and hydrogen, in which mixture the hydrogen:aldehyde molar ratio lies in the range of from about 2:1 to about 100:1;
   (ii) continuously feeding said hydrogenation mixture to a catalytic aldehyde hydrogenation zone containing a charge of a hydrogenation catalyst comprising a reduced mixture of copper oxide and zinc oxide and maintained at a temperature in the range of from about 75° C. to about 300° C. and at a pressure in the range of from about 5 kg/cm² absolute to about 50 kg/cm² absolute;
   (iii) recovering a product mixture comprising a major amount of product alcohol, a minor amount of by-product ester containing twice as many carbon atoms as the aldehyde and derived from an alkyl carboxylic acid containing the same number of carbon atoms as the product alcohol and from the product alcohol, and excess hydrogen;
   (iv) recycling excess hydrogen to step (i)
   (v) separating by-product ester from product alcohol;
   (vi) supplying make-up hydrogen containing gas;
   (vii) vaporizing by-product ester from step (v) in make-up hydrogen containing gas of step (vi) to form a vaporous mixture containing by-product ester and hydrogen in excess of the stoichiometric amount required to effect hydrogeneolysis of said ester to form, per mole of ester, 2 moles of product alcohol, the vapor pressure of said by-product ester in said vaporous mixture being at least about 0.2 kg/cm²;
   (viii) contacting said vaporous mixture from step (vii) in a secondary catalytic hydrogenation zone with a catalyst consisting essentially of a reduced mixture of copper oxide and zinc oxide, said secondary catalytic hydrogenation zone being maintained at a temperature of from about 160° C. to about 220° C. and at a pressure of from bout 5 kg/cm² absolute to about 50 kg/cm² absolute; and
   (ix) admixing a resulting mixture consisting of excess hydrogen and product alcohol from the secondary catalytic hydrogenation zone with the product mixture of step (iii), whereby express hydrogen from the secondary catalytic hydrogenation zone provides make-up hydrogen for the catalytic aldehyde hydrogenation zone.

14. A process according to claim 13, in which the aldehyde is selected form n-butyraldehyde, iso-butyraldehyde, and mixtures thereof; the by-product ester is selected from n-butyl butyrate, iso-butyl butyrate, n-butyl iso-butyrate and iso-butyl iso-butyrate, and mixtures thereof; and the product alcohol is selected from n-butanol, iso-butanol, and mixtures thereof.

15. A process according to claim 13, in which the aldehyde is propionaldehyde; the by-product ester is n-propyl propionate, and the product alcohol is n-propanol.

16. A process according to claim 13, in which the aldehyde is 2-ethylpropylacrolein, the by-product ester is 2-ethylhexyl 2-ethylhexanoate, and the product alcohol is 2-ethylhexanol.

17. In a continuous process for the production of an aliphatic alcohol containing 2 to 10 carbon atoms by catalytic hydrogenation of an aliphatic aldehyde containing 2 to 10 carbon atoms by reaction of a hydrogenation mixture containing the aldehyde and hydrogen in a catalytic aldehyde catalyst effective for the hydrogenation of aldehydes and maintained under aldehyde hydrogenation conditions, followed by recovery of a reaction mixture containing, in addition to product alcohol, a minor amount of a by-product ester containing twice as many carbon atoms as the product alcohol, said ester being derived from an alkyl carboxylic acid containing the same number of carbon atoms at the product alcohol and from the product alcohol, the improvement comprising separating by-product ester from the reaction mixture, and passing an essentially aldehyde-free vaporous mixture comprising by-product ester and hydrogen, in which mixture the vapour pressure of said by-product ester is at least about 0.05 kg/cm² over a catalyst consisting of a reduced mixture of copper oxide and zinc oxide and from 0 to 20 percent by weight of at least one carrier material, in a secondary catalytic hydrogenation zone, at a temperature in the range of from about 150° C. to about 240° C. and at a pressure in the range of from about 5 kg/cm² absolute up to bout 50 ,kg/cm² absolute, and recovering from said secondary catalytic hydrogenation zone a reaction mixture that is substantially free from by-product ester and contains a substantially quantitative yield of further product alcohol corresponding to 2 moles of further product alcohol per mole of by-product ester treated in the secondary catalytic hydrogenation zone.

* * * * *

UNITED STATES PATENT AND TRADEMARK OFFICE
CERTIFICATE OF CORRECTION

PATENT NO. : 5,004,845
DATED : April 2, 1991
INVENTOR(S) : Michael W. Bradley et al.

It is certified that error appears in the above-identified patent and that said Letters Patent is hereby corrected as shown below:

Column 13, line 47, "mentioned" should be --monitored--.

Column 16, line 9, "express" should be --excess--.

Column 16, line 34, after "aldehyde" insert --hydrogenation zone containing a charge of a hydrogenation--.

Column 16, line 53, "bout" should be --about--.

Column 16, line 54, delete the comma "," (first occurrence).

Signed and Sealed this

Eighth Day of June, 1993

Attest:

MICHAEL K. KIRK

*Attesting Officer*  *Acting Commissioner of Patents and Trademarks*